United States Patent [19]

Robinson et al.

[11] Patent Number: 5,643,751
[45] Date of Patent: Jul. 1, 1997

[54] *BORRELIA BURGDORFERI* ANTIGENS AND USES THEREOF

[75] Inventors: John M. Robinson, Gurnee; Tami J. Pilot-Matias, Libertyville; Jeffrey C. Hunt, Lindenhurst, all of Ill.

[73] Assignee: Abbott Laboratories, Abbott Park, Ill.

[21] Appl. No.: 500,125

[22] Filed: Jul. 10, 1995

Related U.S. Application Data

[62] Division of Ser. No. 779,704, Oct. 21, 1991.

[51] Int. Cl.$^6$ ............................ C12P 21/06; C12N 15/00; C12N 15/09; C12N 15/63
[52] U.S. Cl. .................. 435/69.1; 435/69.3; 435/69.7; 435/172.3; 435/320.1; 935/22; 935/38
[58] Field of Search .................. 435/69.1, 69.3, 435/172.3, 69.7, 320.1; 935/22, 38

[56] References Cited

U.S. PATENT DOCUMENTS 5,124,255  6/1992  Bolling et al. .................. 435/69.3

OTHER PUBLICATIONS

Journal of Bacteriology, vol. 173, No. 4, Feb. '91, G. S. Gassmann et al., "Analysis of the *Borrelia burgdorferi* GeHo fla Gene and Antigenic Characterization of Its Gene Product" pp. 1452–1459.

Infection and Immunity, vol. 52, No. 5, May 1986, A.G. Barbour et al., "A Borrelia–Specific Monoclonal Antibody Binds to a Flagellar Epitope", pp. 549–554.

Nucleic Acids Research, vol. 17, No. 9, 1989, G.S. Gassmann et al., "Nucleotide sequence of a gene encoding the *Borrelia burgdorferi* flagellin", pp. 3590–3535.

Infection and Immunity, vol. 59, No. 10, Oct. 1991, R. Berland, et al., "Molecular Characterization of the Humoral Response to the 41–Kilodalton Flagellar Antigen of *Borrelia burgdorferi*, the Lyme Disease Agent", pp. 3531–3535.

Infection and Immunity, vol. 58, No. 6, Jun. 1990, R. Wallich et al., "The *Borrelia burgdorferi* Flagellum–Associated 41–Kilodalton Antigen (Flagellin): Molecular Cloning, Expression, and Amplification of the Gene", pp. 1711–1719.

Infection and Immunity, vol. 59, No. 2, Feb. 1991, C. Collins et al., "Immunoactive Epitopes on an Expressed Recombinant Flagellar Protein of *Borrelia burgdorferi*", pp. 514–520.

E. Harlow, et al., Antibodies A Laboratory Manual, Cold Spring Harbor Laboratory, 1988, pp. 590, 567–569, 583–584.

J. Sambrook, et al., Molecular Cloning, A Laboratory Manual, Cold Spring Harbor Laboratory Press, 1989, pp. 17.2–17.9.

New England Nuclear Catalog, 1983, pp. 139–140.

Maniatis et al "Molecular Cloning" Cold Spring Harbor Laboratory, pp. 504–506, 1982.

*Primary Examiner*—James C. Housel
*Assistant Examiner*—Rodney P. Swartz
*Attorney, Agent, or Firm*—Cheryl L. Becker; David L. Weinstein

[57] ABSTRACT

This invention relates generally to an assay for Lyme disease which detects the antibody to *Borrelia burgdorferi*, the causative agent of Lyme disease. More specifically, the assay employs antigens derived from amino acid regions in the flagellum of *Borrelia burgdorferi*. These antigens are immunoreactive with antibodies to *Borrelia burgdorferi* but are not substantially immunoreactive with antibodies to *Treponema pallidum*, the syphilis causing agent. DNA sequences of the antigens, clones and vectors containing the DNA sequences are also disclosed. Polypeptides derived therefrom can be used as reagents for the detection of antibody to *Borrelia burgdorferi* in the body fluids from individuals with Lyme disease.

20 Claims, 12 Drawing Sheets

The character to show that two aligned residues are identical is '*'

```
FLA$BORBU  - MIINHNTSAINASRNNGINAANLSKTQEKLSSGYRINRASDDAAGMGVSG  -50
             ******  *           *  ******* ****   *  **
TRPPAFLAB2 - MIINHNMSAMFSQRTLGHTNLSVQKNIEKLSSGLRINRSGDDASGLAVSE -50

FLA$BORBU  - KINAQIRGLSQASRNTSKAINFIQTTEGNLNEVEKVLVRMKELAVQSGNG  -100
             *  ***** ***  *     *** *  *    *   *  ** **
TRPPAFLAB2 - KMRSQIRGLNQASTNAQNGISFIQVAEAFLQETTDVIQRIRELSVQAANG -100

FLA$BORBU  - TYSDADRGSIQIEIEQLTDEINRIADQAQYNQMHMLSNKSASQNVRTAEE -150
             **  **  **  *   ***  *** ** ** * **    *
TRPPAFLAB2 - IYSAEDRLYIQVEVSQLVAEVDRIASHAQFNGMNMLTGRFARQG----- -144

FLA$BORBU  - LGMQPAKINTPASLSGSQASWTLRVHVGANQDEAIAVNIYAANVANLFSG -200
                                        * ***  *
TRPPAFLAB2 - ----------GENTVTASMWFHIGANMDQRTRAYIGTMTAV-------- -175
```

FIG. 1A

```
FLA$BORBU  - EGAQTAQAAPVQEGVQQEGAQQPAPATAPSQGGVNSPVNVTTTVDANTSL  -250
                                 *                *     **
TRPPAFLAB2 - -----------------------------------AMGIRDAGDESVMNIDSPEKANRAI -200

FLA$BORBU  - AKIENAIRMISDQRANLGAFQNRLESIKDSTEYAIENLKASYAQIKDATM  -300
              ** * *** *** ****          * *** *** * *  *
TRPPAFLAB2 - GTLDQAIKRINKQRADLGAYQNRLDHTVAGINVAAENLQAAESRIRDVDM  -250

FLA$BORBU  - TDEVVAATTNSILTQSAMAMIAQANQVPQYVLSLLR  -336
              * ** ** ** ** ****** * ******
TRPPAFLAB2 - AKEMVDYTKNQILVQSGTAMLAQANQATQSVLSLLR  -286
```

FIG. 1B

B. burgdorferi Genomic DNA

Primers
Sense: 5' AAATAGATCTCAGACCCGAGAAATACTTCAAAGGCTAT 3'
Antisense: 5' GGGCAAGCTTATTAACTATTAGTTGTTGCTGCTAC 3'

PCR Amplify
(using "tailed" primers)

776 bp Fla Fragment
BglII          HindIII

Digest with
BglII & HindIII
LIGATION pTPM 210
CKS
BglII
HindIII

Digest with
BglII & HindIII pB776
CKS
776

FIG. 3

Primers
Sense:    5' AAATAGATCTCAGACCCGTCAAACAAATCTGCTTCTCA 3'
Antisense: 5' GGGCAAGCTTATTAATCACTTATCATTCTAATAG 3'

*B. burgdorferi* Genomic DNA

PCR Amplify (using "tailed" primers)

410 bp Fla Fragment

BglII          HindIII

Digest with BglII & HindIII

LIGATION pTPM210 — CKS, BglII, HindIII

Digest with BglII & HindIII pB 410 — CKS, 410

FIG. 5

Primers

Sense: 5' AAATAGATCTCAGACCCGATGATTATCAATCATAATAC 3'
Antisense: 5' GGGCGGTACCTTATTATCTAAGCAATGACAAAAC 3'

FIG. 6

B. burgdorferi Genomic DNA

Primers
Sense: 5' AAATAGATCTCAGACCCGATGATTATCAATCATAATAC 3'
Antisense: 5' GGGCGGTACCTTATTATGATAACATGTGCATTTGGTT 3'

PCR Amplify (using "tailed" primers)

445 bp Fla Fragment
BglII — KpnI

Digest with BglII & KpnI

LIGATION pTB210 (CKS, BglII, KpnI) — Digest with BglII & KpnI pBT445 (CKS, 445)

FIG. 7

Primers
Sense: 5' AAATAGATCTCAGACCCGGATCAAAGGGCAAATTTAGG 3'
Antisense: 5' GGGCGGTACCTTATTATCTAAGCAATGACAAAAC 3'

FIG. 8

BORRELIA BURGDORFERI ANTIGENS AND USES THEREOF

This is a division of U.S. patent application Ser. No. 07/779,704 filed Oct. 21, 1991

DESCRIPTION OF THE BACKGROUND ART

Lyme disease is a multisystem illness caused by the tick-transmitted spirochete *Borrelia burgdorferi* (hereinafter referred to as "*B. burgdorferi*") (Burgdorfer, et al. 1982. Science 216:1317–1319; Steere, et al. 1983. N Engl J Med 308:733–740). Lyme borreliosis is the most common arthropod-borne infection in the United States and has been reported in many countries throughout Asia and Europe (Steere 1989. N Engl J Med 1:586–596). The early feature of the disease is a local infection of the skin, which may be followed by the development of systemic disease involving the nervous system, heart and joints (Steere 1989. N Engl J Med 1:586–596).

Culture of the spirochete from human body fluids and antigen detection methods often are falsely negative in the diagnosis of Lyme disease (Steere, et al. 1983. N Engl J Med 308:733–740; Benach, et al. 1983 N Engl J Med 308:740–742), leaving serological methods for antibodies to *B. burgdorferi* as the most appropriate currently available means for diagnosis. Most current diagnostic assays for Lyme disease utilize whole or sonicated *B. burgdorferi* cells as the test antigen, although many investigators have demonstrated improved performance of these tests when subcellular fractions of the spirochete were used (Grodzicki, et al. 1988. J Infect Dis 157:790–797; Magnarelli, et al. 1989. J Infect Dis 159:43–49; Karlsson, et al. 1990. Eur J Clin Microbiol Infect Dis 9:169–177).

The flagellar protein is an immunodominant protein that generally elicits the earliest immune response after infection (Craft, et al. 1986. Clin Invest 78:934–939; Dattwyler, et al. 1989. Rev Infect Dis 11:1494–1498). Flagellin-enriched fractions of *B. burgdorferi* have been shown to improve the performance of Lyme diagnostic assays (Hansen, et al. 1988. J Clin Microbiol 26:338–346). The specificity of these assays, however, may be reduced because of cross-reactivity of *B. burgdorferi* flagellum with the flagella of other spirochetes, most notably with *Treponema pallidum* (hereinafter referred to as "*T. pallidum*"), the causative agent of syphilis (Magnarelli, et al. 1987. J Infect Dis 156:183–188). Current Lyme disease immunoassays utilize solubilized *B. burgdorferi* as the source of antigen, leading to false positive reactions from individuals with certain conditions, including syphilis, leptospirosis and other spirochetal infections. The lack of specificity is due to the fact that these organisms express similar antigens, especially the highly conserved flagellin protein. Thus, most Lyme disease immunoassays suffer from false positive reactions when syphilis positive patients are analyzed. Many institutions determine syphilis serologic status on all Lyme positive patients; if they are positive for syphilis they are considered to be negative for Lyme disease. This cross-reactivity with syphilis patients can be reduced by adsorption of the patient sera with the Reiter strain of Treponema (Magnarelli, et al. 1990. J Clin Microbiol 28:1276–1279), but this decreases the sensitivity of Lyme diagnostic assays.

The nucleotide and amino acid sequences have been determined for the flagellin protein of several *B. burgdorferi* isolates (Gassmann, et al. 1989. Nucleic Acids Res 17:3590; Wallich, et al. 1990. Infect Immun 58:1711–1719; Gassmann, et al. 1991 J Bacteriol 173:1452–1459; Collins, et al. 1991. Infect Immun 59:514–520). The entire flagellin protein contains 336 amino acids. Comparison of the conserved sequences with that of the *T. pallidum* endoflagellar protein (Pallesen, et al. 1989. Infect Immun 57:2166–2172) indicated high sequence homology at each end of the protein, but more variability in the central region. Collins, et al demonstrated that antibodies in the sera of Lyme and arthritis patients bound exclusively at the common amino-terminal region of the flagellin protein.

Wallich, et al., supra, merely speculated that the center region may be specific, based on comparison of amino acid sequences from similar organisms. Gassman, et al., (J. Bacteriol. 1991. 173:1452–1459) synthesized a series of overlapping octapeptides representing the entire sequence of the flagellum and analyzed serum from animals immunized with a variety of closely related bacteria. They demonstrated that the middle region from amino acid 180 to 260 only bound *B. burgdorferi* serum. Neither group demonstrated specificity using human sera. Significantly, Collins et al, supra observed that most Lyme patient sera bound to the amino-terminus region and their results indicated that a specific assay using flagellin was not possible.

BRIEF SUMMARY OF THE INVENTION

One aspect of the present invention presents improved immuno-assays for detecting the presence of an antibody to a *B. burgdorferi* antigen in a sample by contacting the sample with a "differentiating polypeptide" which binds an antibody to *B. burgdorferi* but which does not substantially bind an antibody to *T. pallidum*. The sample is preferably biological fluids such as whole blood, serum, plasma, cerebral spinal fluid, or synovial fluid.

Another aspect of the invention presents the differentiating polypeptides. The differentiating polypeptides are preferably based on amino acid sequences in the *B. burgdorferi* flagellum, wherein the amino acid sequence is immunoreactive with antibodies to *B. burgdorferi* but is not substantially immunoreactive with antibodies to *T. pallidum*. The differentiating polypeptides are preferably produced by chemical synthesis or recombinantly. Examples of the differentiating polypeptide are: p410, p776, fusion protein p410, fusion protein p776, and equivalent polypeptides thereof. The differentiating polypeptdies may be labelled to facilitate detection in an assay.

Another aspect of the invention presents nucleotide sequences, vectors, and plasmids coding for the differentiating polypeptides, and cells transformed by these plasmids. Processes for recombinantly producing these differentiating polypeptides are also presented.

A further aspect of the invention presents assay kits utilizing the differentiating polypeptides for diagnosing Lyme disease and differentiating it from syphilis.

Other aspects and advantages of the invention will be apparent to those skilled in the art upon consideration of the following detailed description which provides illustrations of the invention in its presently preferred embodiments.

BRIEF DESCRIPTION OF DRAWINGS

FIG. 1 illustrates the sequence homology between the *Borrelia burgdorferi* flagellar protein and the *Treponema pallidum* flagellar protein.

FIG. 3 illustrates the construction of plasmid pB776.

FIG. 5 illustrates the construction of plasmid pB410.

FIG. 6 illustrates the construction of plasmid pBT1042.

FIG. 7 illustrates the construction of plasmid pBT445.

FIG. 8 illustrates the construction of plasmid pBT259.

DETAILED DESCRIPTION OF THE INVENTION

Figure 2:
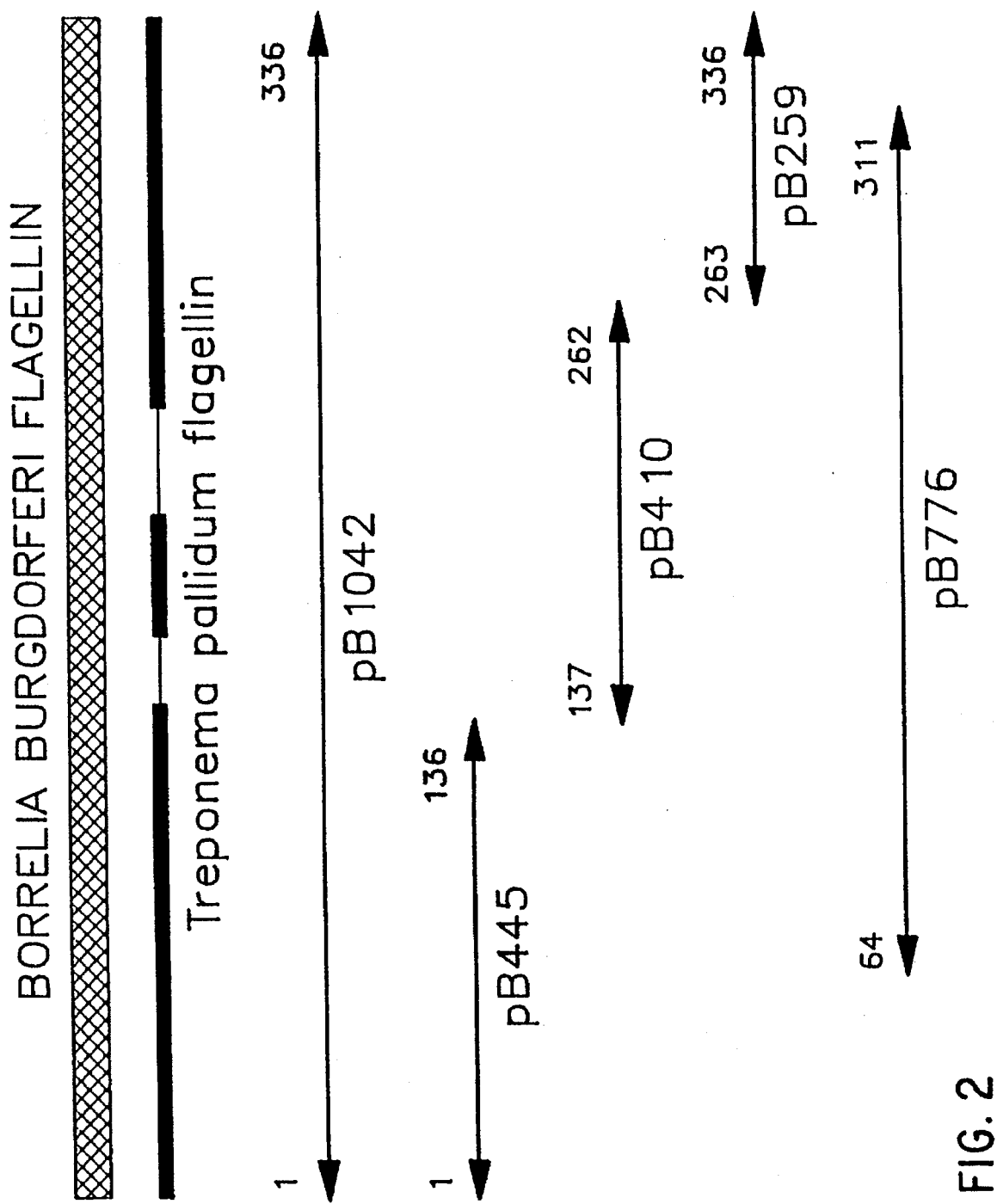
FIG. 2 illustrates the regions of the flagellum protein chosen for cloning and their designations.

This invention provides for differentiating polypeptides which can increase the specificity of Lyme immunoassays without compromising their sensitivity, without the use of Treponema adsorbants, thus increasing the confidence in the results obtained. The differentiating polypeptides bind antibodies to B. burgdorferi but do not substantially bind antibodies to T. pallidum. Preferably, the differentiating polypeptides react with all Lyme positive sera that are reactive with the full length flagellin, yet do not substantially react with syphilis positive sera.

The differentiating polypeptides are preferably recombinant polypeptides that represent distinct antigenic regions of the B. burgdorferi genome. Production of these recombinant flagellin proteins can easily be scaled up to high levels. These recombinant polypeptides can be derived from the molecular cloning and expession of synthetic DNA sequences in heterologous hosts. Specifically disclosed are two recombinant proteins within the immunogenic region of the B. burgdorferi flagellum. Both proteins are expressed as chimeric fusions with the E. coli CMP-KDO synthetase (CKS) gene. The proteins are p410 and p776 expressed by plasmids pB410 and pB776 representing amino acids 137 to 262, and 64 to 311 of the B. burgdorferi sequence, respectively. Note that the terms p410, p776 will also refer to the respective fusion proteins. This invention also covers polypeptides from amino acids about 137 to 262, and 64 to 311, of the B. burgdorferi sequence, which may be prepared using other recombinant or synthetic methodologies. Other recombinant methodologies would include different expression systems. Other synthetic methodologies would include synthetic peptides and synthetic DNA sequences.

Also within the scope of the differentiating polypeptides are "equivalent polypeptides" which include: 1) fragments of p410 and p776 which retain the ability to bind B. burgdorferi antibodies and to differentiate the antibodies from antibodies to T. pallidum; 2) polypeptides which contain changes in amino acid residues of the disclosed amino acid sequences which do not affect the polypeptides' ability to bind B. burgdorferi antibodies and to differentiate the antibodies from antibodies to T. pallidum. Generally, antibodies bind to epitopes defined by about 3 to 10 amino acids. Therefore, certain fragments of p410 and p776 are predicted to bind antibodies to B. burgdorferi more strongly than antibodies to T. pallidum. This is borne out by the comparable reactivity of the Lyme patient sera with p776 and p410, the latter being a fragment of p776. Further, minor amino acid changes in flagellin sequence occur in various B. burgdorferi strains. For example, the American strain B31 (used in the Examples of this application), sequenced by Wallich et al., supra, is different from the European strain GeHo, sequenced by Gassman, et al., supra, at residues 180 and 279. Thus, within the scope of this invention are conservative amino acid changes which do not impair the ability of the resulting polypeptide to differentiate between antibody to B. burgdorferi and antibody to T. pallidum.

The preferred recombinant polypeptides having B. burgdorferi selective antigenic epitopes were selected from portions of the B. burgdorferi flagellum sequence which possess amino acid sequences unique to this organism and which possess little homology to amino acid sequences of other organisms of infectious diseases, such as the flagellum of T. pallidum.

The polypeptides useful in the practice of this invention are preferably produced using recombinant technologies. The DNA sequences which encode the desired polypeptides are amplified by use of the polymerase chain reaction (hereinafter referred to as "PCR"). Oligonucleotide sequences to be used as primers which can specifically bind to the ends of the regions of interest are synthesized. After the desired region of the gene has been amplified the desired sequence is incorporated into an expression vector which is transformed into a host cell. The DNA sequence is then expressed by the host cell to give the desired polypeptide which is harvested from the host cell. Plant, bacterial, yeast, insect, and mammalian expression systems may be used. Vectors which may be used in these expression systems may contain fragments of plant, bacterial, yeast, insect, viral, and/or mammalian origins.

A preferred expression method utilizes a fusion system where the recombinant B. burgdorferi proteins are expressed as a fusion protein with an E. coli enzyme, CKS (CTP:CMP-3-deoxy-manno-octulosonate cytidylyl transferase or CMP-KDO synthetase). The CKS method of protein synthesis is disclosed in published European Published Patent Application No. 331,961 to Bolling, hereby incorporated by reference.

The amplified regions of the B. burgdorferi flagellin gene are digested with appropriate restriction enzymes, ligated and cloned into the CKS fusion vector pTB210 or pTPM210. These plasmids are then transformed into competent E. coli cells. The resultant fusion proteins are under control of the lac promoter.

These differentiating polypeptides can be used for the detection of antibodies against B. burgdorferi in biological fluids. These differentiating polypeptides are preferably used in the serologic detection of Lyme disease, for example, in an enzyme immunoassay format. In an example of a direct assay, these differentiating polypeptides serve as antigens and are attached to a solid phase and then incubated with patient sera. Human serum or plasma is preferably diluted in a sample diluent before incubation. If antibodies to B. burgdorferi are present in the sample they will form an antigen-antibody complex with the differentiating polypeptides and become affixed to the solid phase.

After the antigen-antibody complex has formed, unbound materials and reagents are removed by washing the solid phase and the antigen- antibody complex is reacted with a solution containing labelled antibodies directed against human antibodies. For example, the labelled antibody can be horseradish peroxidase-labeled goat antibody. This peroxidase labeled antibody then binds to the antigen-antibody complex already affixed to the solid phase. In a final reaction the horseradish peroxidase is contacted with o-phenylenediamine and hydrogen peroxide which results in a yellow-orange color. The intensity of the color is proportional to the amount of antibody which initially binds to the differentiating polypeptide affixed to the solid phase.

Another assay format provides for an antibody-capture assay in which anti-immunoglobulin antibody on the solid phase captures the patient's antibody, which is then reacted with the differentiating polypeptide. The application of this format in the serological assay of Lyme disease using prior art antigenic materials is taught in Berardi et al. 1988. J Infect Dis 158:754–760. If antibody to B. burgdorferi is present, it captures the differentiating polypeptide, and the bound differentiating polypeptide is detected by means of labelled polyclonal or monoclonal antibodies directed against the differentiating polypeptides. The antibody-capture assay is particularly useful for and can increase the sensitivity of detection of IgM and IgG to B. burgdorferi antigens. In an example of this assay, the fluid sample is first contacted with a solid support containing a bound antibody capable of binding the mu-chain of IgM or the gamma-chain of IgG antibodies. Specific antibody is detected by reacting this with the differentiating polypeptides followed by non-human antibody to the differentiating polypeptides. The non-human antibody is generally labelled for detection. It is believed that this antibody-capture immunoassay format will have increased sensitivity, especially for IgM. Alternatively, one can forego the non-human antibody and instead label the differentiating polypeptides for direct detection.

Antibodies to the differentiating polypeptides for use in the above capture assay can be produced using standard procedures known in the arts. For example,. antibodies can be produced by innoculating a host animal such as a rabbit, rat, goat, mouse etc., with the differentiating polypeptides or fragments thereof. Before innoculation, the polypeptides or fragments may be first conjugated with keyhole limpet hemocyanin (KLH) or bovine serum albumin (BSA). After an appropriate time period for the animal to produce antibodies to the polypeptides or fragments, the anti-serum of the animal is collected and the polyclonal antibodies separated from the anti-serum using techniques known in the art. Monoclonal antibodies can be produced by the method described in Kohler and Milstein (Nature, 1975. 256: 495-497) by immortalizing spleen cells from an animal inoculated with the polypeptides or fragments thereof. The immortalization of the spleen cell is usually conducted by fusing the cell with an immortal cell line, for example, a myeloma cell line, of the same or different species as the innoculated animal. The immortalized fused cell can then be cloned and the cell screened for production of the desired antibody.

Another assay format provides for an immunodot assay for identifying the presence of an antibody that is immunologically reactive with a B. burgdorferi antigen by contacting a sample with differentiating polypeptides from B. burgdorferi bound to a solid support under conditions suitable for complexing the antibody with the differentiating polypeptides and detecting the antibody-differentiating polypeptide complex by reacting the complex.

Suitable methods and reagents for detecting an antibody-antigen complex in an assay of the present invention are commercially available or known in the relevant art. For example, the detector antibodies or differentiating polypeptides may be labelled with enzymatic, radioisotopic, fluorescent, luminescent, or chemiluminescent label. These labels may be used in hapten-labelled antihapten detection systems according to known procedures, for example, a biotin-labelled antibiotin system may be used to detect an antibody-antigen complex.

In all of the assays, the sample is preferably diluted before contacting the polypeptide absorbed on a solid support. The samples may be biological fluids such as whole blood, serum, plasma, cerebral spinal fluid, or synovial fluid. Solid support materials may include cellulose materials, such as paper and nitrocellulose; natural and synthetic polymeric materials, such as polyacrylamide, polystyrene, and cotton; porous gels such as silica gel, agarose, dextran and gelatin; and inorganic materials such as deactivated alumina, magnesium sulfate and glass. Suitable solid support materials may be used in assays in a variety of well known physical configurations, including microtiter wells, test tubes, beads, strips, membranes, and microparticles. A preferred solid support for a non-immunodot assay is a polystyrene microwell, polystyrene beads, or polystyrene microparticles. A preferred solid support for an immunodot assay is nitrocellulose or paper.

The present invention also encompasses assay kits containing differentiating polypeptides in a concentration suitable for use in immunoassay. In the kits, the differentiating polypeptides may be bound to a solid support and where needed, the kits may include sample preparation reagents, wash reagents, detection reagents and signal producing reagents.

The nucleotide sequences which code for these proteins are also described. Since nucleotide codons are redundant, also within the scope of this invention are equivalent nucleotide sequences which include: nucleotide sequences which code for the same proteins or equivalent proteins. Also within the scope of the invention are fragments and variations of the nucleotide sequences of SEQ ID NO: 3 and SEQ ID NO: 7, which are capable of coding for a polypeptide which is immunoreactive with an antibody to B. burgdorferi but not substantially immunoreactive with an antibody to T. pallidum.

The synthesis, cloning, and characterization of the recombinant polypeptides as well as the preferred formats for assays using these polypeptides are provided it the following examples.

EXAMPLES

Reagents and Enzymes

Restriction enzymes, T4 DNA ligase, nucleic acid molecular weight standards, X-gal (5-bromo-4-chloro-,3-indonyl-β-D-galactoside), and IPTG (isopropyl-β-D-thiogalactoside), were purchased from New England Biolabs, Inc., Beverly, Mass.; or Bethesda Research Laboratories Life Technologies, Inc., Gaithersburg, Md. Prestained protein molecular weight standards were purchased from Diversified Biotech, Newton Centre, Mass. Acrylamide, N-N'-methylene-bis-acrylamide; N,N,N',N',-Tetramethylethylenediamine (TEMED), horseradish peroxidase labeled secondary antibodies, and sodium dodecylsulfate were purchased from BioRad Laboratories, Richmond, Calif. Lysozyme, ampicillin, and tetracycline were obtained from Sigma Chemical Co., St. Louis, Mo.

Superbroth contained gram/L tryptone, 20 gram/L yeast extract, 5 gram/L NaCl, pH 7.4. SDS/PAGE loading buffer consisted of 62.5 mM Tris, pH6.8, 2% SDS, 10% glycerol, 5% 2-mercaptoethanol, and 0.1 mg/ml bromophenol blue. Sonication buffer contained 5 OmM Tris, pH8.0, 5 OmM NaCl, and 1 mM EDTA, Blocking solution consisted of 5% Carnation nonfat dry milk in Tris-buffered saline.

BSKII medium was prepared according to Barbour 1984. Yale. J Biol. Med 57:521–525.

General Methods

All restriction enzyme digestions were performed according to suppliers' instructions. At least 5 units of enzyme were used per microgram of DNA, and sufficient incubation was allowed to complete digestion of DNA. Standard procedures were used for minicell lysate DNA preparation, phenol-chloroform extraction, ethanol precipitation of DNA, restriction analysis of DNA on agarose, low melting agarose gel purification of DNA fragments, and ligation of DNA fragments with T4 DNA ligase (Maniatis et al., *Molecular Cloning. A Laboratory Manual* [New York: Cold Spring Harbor, 1982]).

Example 1

Cloning strategy for specific flagellar protein regions

The amino acids of the *B. burgdorferi* flagellar protein and the flagellar protein of *T. pallidum* were aligned (FIG. 1) using the PALIGN program (PC-Gene; Intelligenetics, Inc., Mountain View, Calif.). The *T. pallidum* flagellar protein has a 38% homology with the *B. burgdorferi* flagellum protein amino acid sequence. This homology is greatest at the amino- and carboxy-termini of each protein, providing for greater heterogeneity in the central region. The *B. burgdorferi* flagellar protein was divided into three regions for cloning based on this homology (FIG. 2); the fragment of amino acid residues 1-136 exhibits 52% homology, the fragment of amino acids 137-262 exhibits 14% homology, and the fragment of amino acids 263-336 exhibits 53% homology with the *T. pallidum* flagellar protein sequence. An additional fragment, encompassing the amino acid residues 64–311 of the *B. burgdorferi* flagellin was chosen for cloning because it was the largest fragment with the least possible homology, exhibiting 30% homology. The common amino acid sequences between these two proteins in region pB445 (containing amino acids 1–136) and pB259 (containing amino acids 263–336) frequently occur in stretches of up to six consecutive residues, while the common amino acid sequences in p410 (containing amino acids 137–262) and p776 (containing amino acids 64–311) are infrequently clustered. This fact is significant because an antibody can potentially recognize stretches of 6 to 8 amino acids.

Example 2

Construction of pB776

A. Construction of Plasmids pTB210 and pTPM210

The CKS expression vector pTB210 allows the fusion of recombinant proteins to the CMP-KDO synthetase (CKS) protein. The vector consists of the plasmid pBR2 with a modified lac promoter fused to a kdsB gene fragment (encoding the first 239 of the entire 248 amino acids of the *E. coli* CMP-KDO synthetase protein), and a synthetic linker fused to the end of the kdsB gene fragment. The synthetic linker includes multiple restriction sites for insertion of genes, translational stop signals, and the trpA rho-independent transcriptional terminator. The vector pTPM210 is identical to pTB210 except for a single mutation in the kdsB gene. This mutation gives rise to a single amino acid change in the CKS protein sequence, Ash at position 239 rather than Asp. The CKS method of protein synthesis as well as CKS vectors including pTB210 are disclosed in European published Patent Application, No. 331,961, to Bolling, which is hereby incorporated by reference.

Preparation of *B. burgdorferi* DNA

DNA was isolated from a 200 ml culture of *B. burgdorferi* strain B31 (ATCC 35210) after 5 days of growth in BSKII medium by the following procedure: Cells were harvested at 3000×g for 15 minutes then resuspended in 8.5 ml of 50 mM glucose, 10 mM EDTA, 25 mM Tris pH 8.0, 2 mg/ml lysozyme. After 15 minutes at room temperature, 1.25 ml of a 4:1 mixture of 20% sarkosyl:0.25M EDTA was added and the solution was mixed gently. This was followed by addition of 9.3 grams of cesium chloride and 0.5 ml of a 5 mg/ml solution of ethidium bromide. The mixture was then centrifuged in a Beckman 70.1 Ti rotor for 40 hours at 44,000 rpm. The DNA band was isolated, extracted with NaCl saturated isopropanol to remove the ethidium bromide, then precipitated with ethanol and resuspended in 10 mM Tris, 1 mM EDTA, pH 8.0.

C. Generation of 776 bp Flagellin Gene Fragment

Oligonucleotide primers for use in the PCR amplification of the region encoding amino acids 64 to 311 of *B. burgdorferi* flagellin were designed based on the published sequence of the gene, and included convenient restriction endonuclease sites to be used for cloning into the CKS expression vectors. The sequences of the primers are shown here:

Sense primer:

5'-AAATAGATCTCAGACCCGAGAAATACTTCAAA-GGCTAT (BglII site is underlined)

Antisense primer:

5'-GGGCAAGCTTATTAACTATTAGTTGTTGCTGCTAC (HindIII site is underlined)

The following were combined in a 0.5 ml microfuge tube and subjected to the amplification cycles shown below: a mixture of 20 mM $(NH_4)_2SO_4$, 80 mM Tris, and 10 mM $MgCl_2$, buffered at pH 9.0; 85 ng *B. burgdorferi* DNA; 60 pMol each primer; 0.4 mM each dATP, dCTP, dGTP, and dTTP; and 2.5 units Taq polymerase. The amplification cycles were 1 cycle of 97° C. for 120 seconds, followed by 4 cycles of 95° C. for 30 seconds, 40° C. for 30 seconds, 72° C. for 60 seconds, followed by 25 cycles of 95° C. for 30 seconds, 65° C. for 90 seconds.

D. Preparation of pB776 Expression Vector

The PCR product generated as described above was digested with BglII and HindIII and cloned into the BglII and HindIII sites of pTPM210 as shown in FIG. 3. The resultant fusion protein, CKS-776, consists of 239 amino acids of CKS, 11 amino acids contributed by linker DNA sequences, and amino acids 64 to 311 of *B. burgdorferi* flagellin. The DNA sequence of the region of pB776 which encodes the CKS-776 recombinant antigen as well as the encoded protein are designated SEQ ID NO: 1 and SEQ ID NO: 2, respectively. The DNA sequence of the flagellin protein region of pB776 and the encoded protein are designated SEQ ID NO:3 and SEQ ID NO: 4, respectively.

The pB776 plasmid was transformed into competent *E. coli* K-12 strain XL-1 Blue (recA1,endA1, gyrA96, thi-1, hsdR17, supE44, relA1, lac, proAB, laclqZDM15, TN10) cells obtained from Stratagene Cloning Systems, La Jolla, Calif. In this construction the expression of the CKS fusion protein was under the control of the lac promoter and was induced by the addition of isopropyl beta-D-thiogalactopyranoside (IPTG). The plasmid replicated as an independent element, was nonmobilizable and was maintained at approximately 10–30 copies per cell.

E. Characterization of Recombinant Flagellin 776 Fragment

In order to establish that clone pB776 expressed the CKS-776 protein, the pB776/XL-1 Blue culture was grown at 37° C. in Superbroth media containing 50 mg/L ampicillin, 15 mg/L tetracycline, and 3 mM glucose. When the culture reached an OD600 of 2.0, a small sample of cells was removed. IPTG was then added to a final concentration of 1 mM to induce expression from the lac promoter.

Another sample was removed after 3 hours of induction and both samples were pelleted, resuspended to an OD600 of 10 in SDS/PAGE loading buffer, and boiled for 5 minutes. Aliquots (5 ul) of the prepared samples were electrophoresed on duplicate 10% SDS/PAGE gels. One gel was stained in a solution of 0.2% Coomassie blue dye in a solution of 40% methanol and 10% acetic acid for 10 minutes. Destaining was carried out using a solution of 16.5% methanol and 5% acetic acid for 3–4 hours, or until a clear background was obtained. The second gel was used for immunoblotting.

Figure 4:
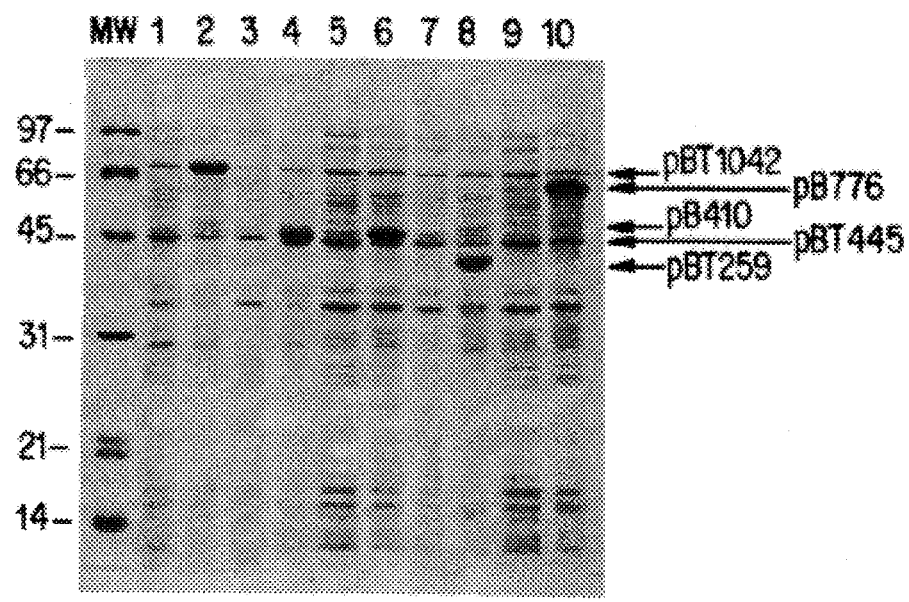
FIG. 4 illustrates the expression of the CKS-flagellum proteins in *E. coli*.
Figure 9:
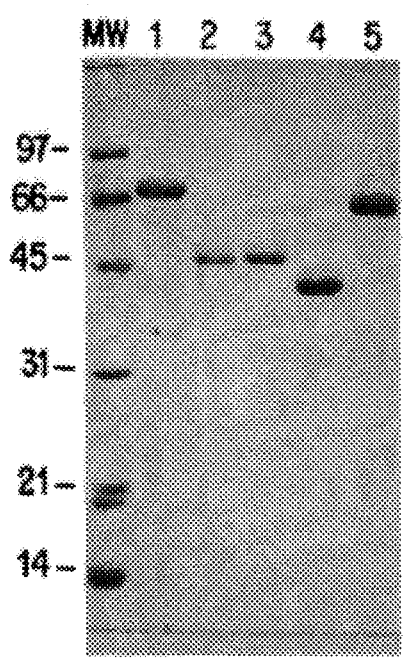
FIG. 9 illustrates the purity of the CKS-flagellum recombinant protein following purification.

FIG. 4 presents the expression of CKS-flagellin proteins in *E. coli*. Lane MW contains molecular weight standards with the sizes shown on the left. The arrows on the right indicates the mobilities of the recombinant CKS-flagellin proteins. Lane 9 contains the *E. coli* lysate expressing CKS-776 prior to induction and lane 10 after 3 hours of induction. The results show that the recombinant protein CKS-776 has a mobility corresponding closely to the predicted molecular mass of 54,070 daltons.

Proteins from the second 10% SDS/PAGE gel were electrophoretically transferred to nitrocellulose for immunoblotting. The nitrocellulose sheet containing the transferred proteins was incubated in blocking solution for 30 minutes at room temperature followed by incubation for 1 hour at room temperature in goat anti-CKS sera which had been preblocked against *E. coli* cell lysate then diluted 1:2000 in blocking solution. The nitrocellulose sheet was washed two times in TBS, then incubated with HRPO-labeled rabbit anti-goat IgG, diluted 1:2000 in blocking solution. The nitrocellulose was washed two times with TBS and the color was developed in TBS containing 2 mg/ml 4-chloro-1-napthol, 0.02% hydrogen peroxide and 17% methanol. Clone pB776 demonstrated a strong immunoreactive band at approximately 54,000 daltons with the anti-CKS sera. Thus, the major protein in the pB776 three hour induced lane on the Coomassie stained gel was the major immunoreactive product as well.

Example 3

Construction of pB410
A. Generation of 410 bp Flagellin Gene Fragment

Oligonucleotide primers for use in the PCR amplification of the region encoding amino acids 137 to 262 of *B. burgdorferi* flagellin were designed based on the published sequence of the gene, and included convenient restriction endonuclease sites to be used for cloning into the CKS expression vectors. The sequences of the primers are shown here:
Sense primer:
5'-AAATAGATCTCAGACCCGTCAAACAAATCTGCTT-CTCA
(BglII site is underlined)
Antisense primer:
5'-GGGCAAGCTTATTAATCACTTATCATTCTAATAG
(HindIII site is underlined)
PCR was performed using these primers and *B. burgdorferi* DNA as described in Example 2.
B. Preparation of pB410 Expression Vector The PCR product generated as described above was digested with BglII and HindIII and cloned into the BglII and HindIII sites of pTPM210 as shown in FIG. 5. The pB410 plasmid was transformed into competent *E. coli* K-12 strain XL-1 Blue as described in Example 2. The resultant fusion protein, CKS-410, consists of 239 amino acids of CKS, 11 amino acids contributed by linker DNA sequences, and amino acids 137 to 262 of *B. burgdorferi* flagellin. The DNA sequence of the region from pB410 encoding the CKS-410 recombinant antigen as well as the encoded protein are designated SEQ. ID. 5 and 6 respectively. The DNA sequence from the *B. burgdorferi* flagellin protein and the encoded protein are designated SEQ. ID. 7 and 8 respectively.

C. Characterization of Recombinant Flagellin 410 Fragment

In order to establish that clone pB410 expressed the CKS-410 protein, the pB410/XL-1 Blue culture was grown and samples were prepared as described in Example 2. FIG. 4 presents the expression of CKS-flagellin proteins in *E. coli*. Lane MW contains molecular weight standards with the sizes shown on the left. The arrows on the right indicates the mobilities of the recombinant CKS-flagellin proteins. Lane 5 contains the *E. coli* lysate expressing CKS-410 prior to induction and lane 6 after 3 hours of induction. The results show that the recombinant protein CKS-410 has a mobility corresponding closely to the predicted molecular mass of 40,440 daltons. Clone pB410 also demonstrated a strong immunoreactive band at approximately 40,000 daltons with the anti-CKS sera when reacted as described in Example 2. Thus, the major protein in the pB410 three hour induced lane on the Coomassie stained gel was the major immunoreactive product as well.

Example 4

Construction of pBT1042
A. Generation of 1042 bp Flagellin Gene Fragment

Oligonucleotide primers for use in the PCR amplification of the region encoding amino acids 1 to 336 of *B. burgdorferi* flagellin were designed based on the published sequence of the gene, and included convenient restriction endonuclease sites to be used for cloning into the CKS expression vectors. The sequences of the primers are shown below:
Sense primer:
5'-AAATTAGATCTCAGACCCGATGATTATCAATCAT-AATAC
(BglII site is underlined)
Antisense primer:
5'-GGGCGGTACCTTATTATCTAAGCAATGACAAAAC
(KpnI site is underlined)
PCR was performed using these primers and *B. burgdorferi* DNA as described in Example 2.
B. Preparation of pBT1042 Expression Vector The PCR product generated as described above was digested with BglII and KpnI and cloned into the BglII and KpnI sites of pTB210 as shown in FIG. 6. The pBT1042 plasmid was transformed into competent *E. coli* K-12 strain XL-1 Blue as described in Example 2. The resultant fusion protein, CKS-1042, consists of 239 amino acids of CKS, 11 amino acids contributed by linker DNA sequences, and amino acids 1 to 336 of *B. burgdorferi* flagellin.

C. Characterization of Recombinant Flagellin 1042 Fragment

In order to establish that clone pBT1042 expressed the CKS-1042 protein, the pBT1042/XL-1 Blue culture was grown and samples were prepared as described in Example 2. FIG. 4 presents the expression of CKS-flagellin proteins in *E. coli*. Lane 1 contains the *E. coli* lysate expressing CKS-1042 prior to induction and lane 2 after 3 hours of induction. The results show that the recombinant protein CKS-1042 has a mobility corresponding closely to the predicted molecular mass of 63,350 daltons. Clone pBT1042 also demonstrated a strong immunoreactive band at approximately 63,000 daltons with the anti-CKS sera when reacted as described in Example 2. Thus, the major protein in the pBT1042 three hour induced lane on the Coomassie stained gel was the major immunoreactive product as well.

Example 5

Construction of pBT445

A. Generation of 445 bp Flagellin Gene Fragment

Oligonucleotide primers for use in the PCR amplification of the region encoding amino acids 1 to 137 of *B. burgdorferi* flagellin were designed and included convenient restriction endonuclease sites to be used for cloning into the CKS expression vectors. The sequences of the primers are shown below:

Sense primer:
5'-AAATAGATCTCAGACCCGATGATTATCAATCATAATAC

BglII site is underlined

Antisense primer:
5'-GGGCGGTACCTTATTATGATAACATGTGCATTTGGTT

KpnI site is underlined

PCR was performed using these primers and *B. burgdorferi* DNA as described in Example 2.

B. Preparation of pBT445 Expression Vector

The PCR product generated as described above was digested with BglII and KpnI and cloned into the BglII and KpnI sites of pTB210 as shown in FIG. 7. The pBT445 plasmid was transformed into competent *E. coli* K-12 strain XL-1 Blue as described in Example 2. The resultant fusion protein, CKS-445, consists of 239 amino acids of CKS, 11 amino acids contributed by linker DNA sequences, and amino acids 1 to 137 of *B. burgdorferi* flagellin.

C. Characterization of Recombinant Flagellin 445 Fragment

In order to establish that clone pBT445 expressed the CKS-445 protein, the pBT445/XL-1 Blue culture was grown and samples were prepared as described in Example 2. FIG. 4 presents the expression of CKS-flagellin proteins in *E. coli*. Lane 3 contains the *E. coli* lysate expressing CKS-445 prior to induction and lane 4 after 3 hours of induction. The results show that the recombinant protein CKS-445 has a mobility corresponding closely to the predicted molecular mass of 42,500 daltons. Clone pBT445 also demonstrated a strong immunoreactive band at approximately 42,000 daltons with the anti-CKS sera when reacted as described in Example 2. Thus, the major protein in the pBT445 three hour induced lane on the Coomassie stained gel was the major immunoreactive product as well.

Example 6

Construction of pBT259

A. Generation of 259 bp Flagellin Gene Fragment

Oligonucleotide primers for use in the PCR amplification of the region encoding amino acids 262 to 336 of *B. burgdorferi* flagellin were designed, and included convenient restriction endonuclease sites to be used for cloning into the CKS expression vectors. The sequences of the primers are shown below:.

Sense primer:
5'-AAATAGATCTCAGACCCGGATCAAAGGGCAAATTTAGG

BglII site is underlined

Antisense primer:
5'-GGGCGGTACCTTATTATCTAAGCAATGACAAAAC

KpnI site is underlined

PCR was performed using these primers and *B. burgdorferi* DNA as described in Example 2.

B. Preparation of pBT259 Expression Vector

The PCR product generated as described above was digested with BglII and KpnI and cloned into the BglII and KpnI sites of pTB210 as shown in FIG. 8. The pBT259 plasmid was transformed into competent *E. coli* K-12 strain XL-1 Blue as described in Example 2. The resultant fusion protein, CKS-259, consists of 239 amino acids of CKS, 11 amino acids contributed by linker DNA sequences, and amino acids 262 to 336 of *B. burgdorferi* flagellin.

C. Characterization of Recombinant Flagellin 259 Fragment

In order to establish that clone pBT259 expressed the CKS-259 protein, the PBT259/XL-1 Blue culture was grown and samples were prepared as described in Example 2. FIG. 4 presents the expression of CKS-flagellin proteins in *E. coli*. Lane 7 contains the *E. coli* lysate expressing CKS-259 prior to induction and lane 8 after 3 hours of induction. The results show that the recombinant protein CKS-259 has a mobility corresponding closely to the predicted molecular mass of 35,820 daltons. Clone pBT259 also demonstrated a strong immunoreactive band at approximately 36,000 daltons with the anti-CKS sera when reacted as described in Example 2. Thus, the major protein in the pBT259 three hour induced lane on the Coomassie stained gel was the major immunoreactive product as well.

Example 7

Production and Purification of CKS-flagellin proteins

The *E. coli* cultures expressing recombinant flagellin proteins were grown overnight at 37° C. in growth media consisting of tryptone, yeast extract, sodium chloride, glucose, tetracycline and ampicillin as described above. When the cultures reached an OD600 of 1.0, IPTG was added to a final concentration of 1 mM to induce expression. After incubation for 4 to 16 hours, the cells were pelleted at 25,000×g and lysed by suspension in a buffer containing 50 mM Tris, pH 8.5, 10 mM EDTA, 1 mg/ml lysozyme and 0.5% Triton X-100, followed by sonication. After centrifugation of the lysed sample, the recombinant proteins are found in the insoluble pellet. These recombinant proteins are produced in the *E. coli* cell as inclusion bodies, and are thus very insoluble. The soluble *E. coli* proteins were then removed from the insoluble protein by a series of washes in various buffers. The lysed cell pellet was first washed in Tris-EDTA buffer containing 5% Triton X-100 followed by washes of 1% sodium deoxycholate and then 0.5M sodium chloride in Tris-EDTA. After a water wash, the CKS-flagellin proteins were solubilized in 8M urea and 1 mM DTT and analyzed by SDS-PAGE as described above in Example 2, subparagraph E. FIG. 9 illustrates the purity of these proteins, Lane MW contains molucular weight standards with the sizes shown on the left. Purified p1042, p445, p410, p259, and p776 are in lanes 1 to 5 respectively.

Example 8

Diagnostic Utility of CKS-Flagellin Recombinant Proteins

Diagnostic Assay: Microtiter Plate Assay

In one embodiment of the present diagnostic assay, recombinant protein coated microtiter wells are used to capture human anti-flagellin antibody. The microtiter plate wells are incubated with 100 ul of a solution containing recombinant CKS-flagellin diluted to 1.0 to 5.0 ug/ml in 0.05M carbonate buffer, pH 9.6. The plates are incubated in the antigen solution for one hour at 37° C., washed in water, and overcoated in a solution consisting of 10% fetal calf serum and 3% gelatin in PBS for 30 minutes at 37° C., followed by a water wash.

Serum samples to be analyzed are diluted 1:200 in a diluent consisting of 100 mM Tris, pH 7.5, 135 mM NaCl, 10 mM EDTA, 0.2% Tween 20, 0.01% thimerosal, 4% fetal calf serum and 1% *E. coli* lysate. After one hour of incubation of 100 ul of the diluted sample per well at 37° C., the plate is washed three times with PBS containing 0.05% Tween 20.

Various enzyme-antibody conjugates are used to detect the presence of antibody in the sample. Goat anti-human IgG, goat anti-human IgM or goat anti-human IgG+IgM+IgA antibodies conjugated to horseradish peroxidase are typically used, but other signal generating enzymes conjugated to these antibodies are also utilized, including alkaline phosphatase and urease. These conjugates are diluted to 0.1 to 0.5 ug/ml in a diluent consisting of 100 mM Tris, pH7.5, 135 mM NaCl, 0.01% thimerosal and 10% fetal calf serum. After one hour incubation of 100 ul of the diluted conjugate per well at 37° C., the plate is washed three times with PBS containing 0.05% Tween 20. The OPD substrate solution is then added to each well and allowed to react for 5 minutes at room temperature and the reaction terminated by the addition of 1N sulfuric acid. The absorbance is then read at 490 nm.

Assay performance of the recombinant proteins with Lyme, syphilis, and normal sera.

Figure 10:
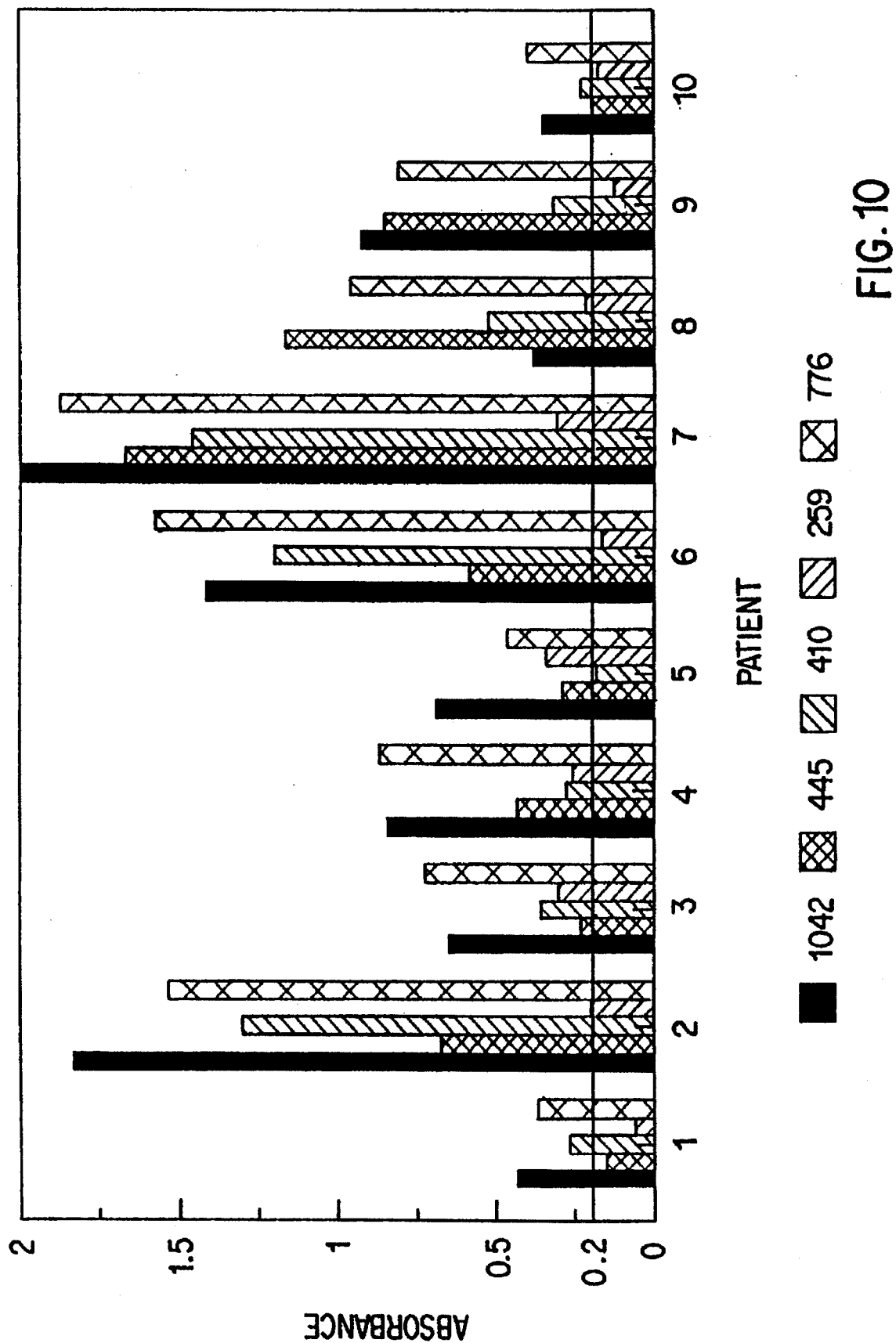
FIG. 10 illustrates the reactivity of the recombinant flagellar proteins with sera from patients with clinical histories of Lyme disease.

The total antibody reactivity of representative Lyme disease positive sera or syphilis positive sera with each of the CKS-flagellin recombinant proteins was evaluated. The total antibody was detected using the goat anti-human IgG+IgM+IgA - horseradish peroxidase conjugate described above in the preceding section. The ten Lyme specimens in FIG. 10 are case history defined positive patients, provided by physicians in endemic areas for Lyme disease from patients clinically diagnosed as having Lyme disease, based on dermatological, neurological, cardiac or arthritic manifestations, as defined for Lyme disease by the Centers for Disease Control.

All of these Lyme positive sera are reactive with the protein encoded by the full length flagellin clone and also are reactive with the p776 and p410 proteins, using a cut-off value of 0.2. Reactivity with the 410 protein is generally weaker than with the full length p1042 protein, yet the p776 protein reactivity is equivalent or greater than with the full length flagellin protein. Nine of these samples were reactive with the p445 protein and seven were reactive with the p259 protein, indicating that the humoral response to the flagellin protein may encompass the entire protein.

Figure 11:
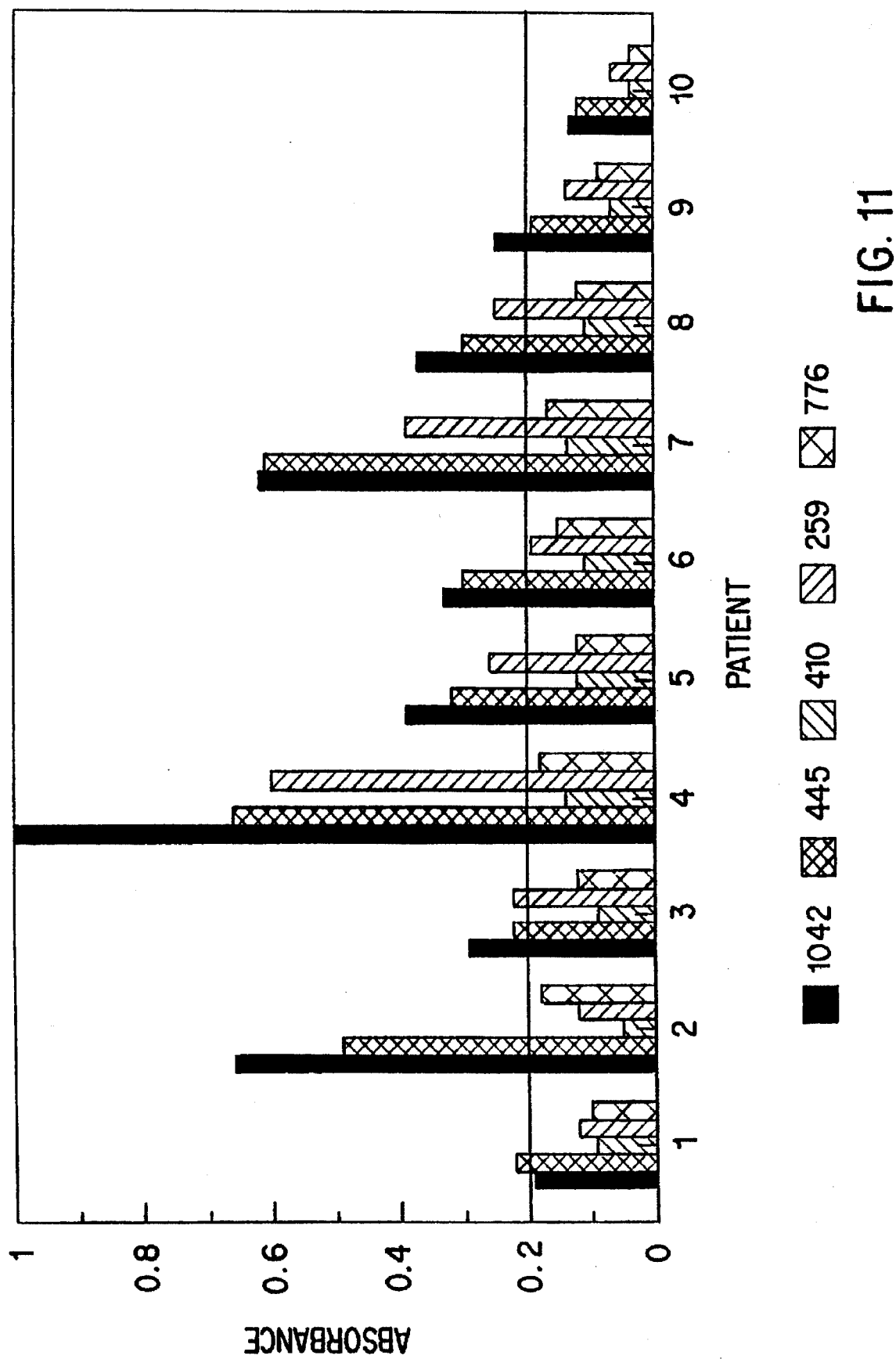
FIG. 11 illustrates the reactivity of the recombinant flagellar proteins with sera from patients with syphilis disease.

Reactivity of these proteins with sera from syphilis positive patients is presented in FIG. 11. These sera were provided by the Centers for Disease Control (CDC) and had been determined to be positive by Rapid Plasma Reagin (PRP), Venereal Disease Research Laboratory (VDRL), and FTA-ABS (Fluorescent Treponemal Antibody Absorption) tests. These tests are routinely performed as described in Coffey and Bradford (*Manual of Clinical Microbiology*, 2nd Ed., 1980, Ch. 74: 530–540) Eight of the sera were reactive with the full length protein and with the amino-terminus region represented by protein p445. This is consistant with the amino acid sequence homology displayed between the *B. burgdorferi* and the *T. pallidum* flagellin proteins in this region. Four of these sera were also reactive with the carboxy-terminus p259 protein. In sharp contrast, none of the sera were reactive with the unique, non-homologous p410 or p776 proteins indicating that these are *B. burgdorferi* specific regions.

Evaluation of a larger population of sera, distinguishing the IgG and the IgM response, is presented in a summary fashion in Tables 1 and 2 below:

TABLE 1

Serum IgG Antibody Reactivity with
CKS-Flagellin Recombinant Proteins
(Number of specimens reactive)
CKS-Flagellin Recombinant Proteins

| SPECIMEN (No.) | p1042 | p445 | p410 | p259 | p776 |
| --- | --- | --- | --- | --- | --- |
| Case history defined Lyme disease (25) | 22 | 18 | 19 | 15 | 22 |
| Western blot-defined Lyme disease (43) | 34 | 31 | 29 | 23 | 33 |
| Syphilis positive (24) | 12 | 10 | 0 | 6 | 1 |
| Normal (37) | 7 | 2 | 0 | 6 | 0 |

TABLE 2

Serum IgM Antibody Reactivity with CKS-Flagellin
Recombinant Proteins (Number of specimens reactive)
CKS-Flagellin Recombinant Proteins

| SPECIMEN (No.) | p1042 | p445 | p410 | p259 | p776 |
| --- | --- | --- | --- | --- | --- |
| Case history defined Lyme disease (16) | 14 | 2 | 12 | 1 | 16 |
| Western blot defined Lyme disease (16) | 14 | 3 | 13 | 0 | 14 |
| Syphilis positive (24) | 0 | 0 | 0 | 0 | 0 |
| Normal (37) | 0 | 0 | 0 | 0 | 0 |

The assays for Tables 1 and 2 are as described above, with the only difference being the detection reagent used. In the IgG assay, the IgG antibody bound to the recombinant protein was detected with a goat anti-human IgG-horseradish peroxidase conjugate, while in the IgM assay the goat anti-human IgM horseradish peroxidase conjugate is used to detect the IgM antibody bound to the recombinant protein. Lyme disease positive sera were divided into two categories based on whether they were patient case history defined positive or were designated Lyme disease positive based on Western blot testing.

Western blotting for the identification of Lyme disease positive patients was similar to that described above. *B. burgdorferi* strain B31 was denatured in SDS/PAGE loading buffer and a volume representing 7.5 mg wet weight of cells electrophoresed on 12% acrylamide PAGE gels. These proteins were electrophoretically transferred to nitrocellulose sheets and blocked overnight in a solution consisting of 100 mM Tris, 135 mM NaCl and 3% gelatin. Serum specimens were diluted 1:50 in the same antibody diluent as described for the microtiter plate assay and allowed to react with the nitrocellulose sheets for two hours. After washing with TBS, the antibody-antigen reactions were detected using the same conjugates, either anti-human IgG or IgM, as described above. The nitrocellulose was washed with TBS and the color developed in TBS containing 2 mg/ml 4-chloro-1-napthol, 0.02% hydrogen peroxide and 17% methanol. A serum specimen was considered positive for IgG antibody if at least five *B. burgdorferi* proteins were reactive, and IgM positive if at least three proteins were reactive.

The IgG antibody reactivity with the recombinant flagellin proteins (Table 1) indicates that the IgG response to flagellin was not restricted to one region, although the p776 protein was recognized by all but one serum specimen that reacted with the full-length protein. Most of the Lyme disease specimens also recognized the p410 protein. Not all of the Lyme positive sera were flagellin reactive, since, depending on the stage of infection, many Lyme patients were seronegative, or the response to the flagellin protein had waned and reactivity with other *B. burgdorferi* proteins occured. As predicted from the sequence homology with *T. pallidum*, many of the RPR positive specimens and some of the normal sera are reactive with amino-terminus of the flagellin represented by protein p445 and with the carboxy-terminal region expressed in protein p259, as well as the full length protein. None of the syphilis positive or normal sera are reactive with the central region of the flagellin protein represented by protein p410, and only one syphilis positive sera shows reactivity with the larger p776 protein, indicating that these regions are specific for Lyme disease. The data indicate that the use of the p410 or p776 protein in an immunoassay can distinguish Lyme disease from syphilis without the use of any pre-absorption steps.

The serum IgM reactivity with the flagellin regions (Table 2) demonstrates that those regions defined by proteins p410 and p776 are most reactive. Of the Lyme disease IgM positive specimens, 30 and 25 were reactive with the p776 and p410 proteins, respectively, indicating that these proteins are useful markers for the detection of early Lyme disease. There was no cross-reactive IgM antibody to any of the flagellin proteins in the syphilis or the normal sera tested. In the case of detection of IgM antibody, the p776 and p410 proteins are far superior to either end of the flagellin protein, indicating that the earliest response in humans to flagellin is elicited by the central unique region.

Deposit

The recombinant transfer vectors pB410 and pB776 in *E. coli* K-12 have been deposited under the Budapest Treaty, at the American Type Culture Collection, Rockville, Md. 20852 (U.S.A.) on Oct. 3, 1991 under the respective ATCC Nos. 68724 and 68725.

Availability of the deposited strains is not to be construed as a license to practice the invention in contravention of the rights granted under the authority of any government in accordance with its patent laws.

Also, the present invention is not to be considered limited in scope by the deposited recombinant transfer vectors, since the deposited vectors are intended only to be illustrative of particular aspects of the invention. Any recombinant transfer vector which can be used to prepare recombinant microorganism which can function to produce a recombinant protein product is considered to be within the scope of this invention. Further, various modifications of the invention in addition to those shown and described herein which are apparent to those skilled in the art from the preceding description are considered to fall within the scope of the appended claims.

BORRELIA BURGDOFERI ANTIGENS AND USES THEREOF

We claim:

1. A nucleotide sequence comprising SEQ ID NO: 7.

2. A nucleotide sequence comprising a sequence selected from the group consisting of SEQ ID NO: 1 and SEQ ID NO: 5.

3. A of nucleotide sequence SEQ ID NO:3 or SEQ ID NO:7 which encodes a polypeptide which binds an antibody to *B. burgdorferi*, but which does not bind an antibody to *T. pallidum*.

4. A vector comprising a nucleotide sequence selected from the group consisting of SEQ ID NO: 3, and SEQ ID NO: 7, wherein said nucleotide sequence encodes a polypeptide which binds an antibody to *B. burgdorferi*, but does not bind an antibody to *T. pallidum*.

5. Plasmid pB776.

6. Plasmid PB410.

7. A host transformed by a nucleotide sequence selected from the group consisting of SEQ ID NO: 3, and SEQ ID NO: 7, wherein said nucleotide sequence encodes a polypeptide which binds an antibody to *B. burgdorferi*, but does not bind an antibody to *T. pallidum*.

8. The transformed cell of claim 7, selected from the group consisting of a plant cell, a bacterial cell, a yeast cell, an insect cell, and a mammalian cell.

9. A transformed cell which produces a non-naturally occurring polypeptide which binds an antibody to *B. burgdorferi*, but does not bind an antibody to *T. pallidum*, wherein said polypeptide comprises an amino acid sequence selected from the group consisting of SEQ ID NO:4 and SEQ ID NO: 8.

10. The transformed cell of claim 9, wherein said cell is selected from the group consisting of a plant cell, a bacterial cell, a yeast cell, an insect cell, and a mammalian cell.

11. A transformed cell capable of producing a polypeptide comprising the amino acid sequence of claim 9, wherein said sequence retains the ability to bind an antibody to *B. burgdorferi* and to differentiate between the antibody to *B. burgdorferi* and the antibody to *T. pallidum*.

12. The transformed cell of claim 11, selected from the group consisting of plant, bacteria, yeast, insect, and mammal.

13. Transformed *E.coli* designated ATCC No. 68724 or ATCC No. 68725.

14. A process for producing a polypeptide specific for *B. burgdorferi*, comprising the steps of:

a) introducing into a host cell, a vector containing a nucleotide sequence encoding said polypeptide, said nucleotide sequence being selected from the group consisting of SEQ ID NO: 3, and SEQ ID NO: 7, wherein said polypeptide binds an antibody to *B. burgdorferi*, but does not bind an antibody to *T. pallidum*, b) culturing said resulting transformed host cell under time and conditions suitable for expression of said polypeptide, and c) harvesting said polypeptide produced by said resulting transformed host cell.

15. A transformed host cell which produces a non-naturally occurring polypeptide which binds an antibody to *B. burgdorferi*, but does not bind an antibody to *T. pallidum*, wherein said polypeptide comprises an amino acid sequence selected from the group consisting of SEQ ID NO:2 and SEQ ID NO:6.

16. The transformed host cell of claim 15, wherein said cell is selected from the group consisting of a plant cell, a bacterial cell, a yeast cell, an insect cell, and a mammalian cell.

17. A transformed cell capable of producing a polypeptide comprising the amino acid sequence of claim 15, wherein said sequence retains the ability to bind an antibody to *B. burgdorferi* and to differentiate between the antibody to *B. burgdorferi* and the antibody to *T. pallidum*.

18. The transformed cell of claim 17, selected from the group consisting of plant, bacteria, yeast, insect, and mammal.

19. A transformed host cell which produces a polypeptide, wherein said polypeptide comprises an amino acid sequence which is recognized by an antibody which binds an amino acid sequence selected from the group consisting of SEQ ID NO:4 and SEQ ID NO:8; wherein said polypeptide binds an antibody to *B. burgdorferi*, but does not bind an antibody to *T. pallidum*.

20. The transformed host cell of claim 19, wherein said cell is selected from the group consisting of a plant cell, a bacterial cell, a yeast cell, an insect cell, and a mammalian cell.

* * * * *

UNITED STATES PATENT AND TRADEMARK OFFICE
CERTIFICATE OF CORRECTION

PATENT NO. : 5,643,751
DATED : July 1, 1997
INVENTOR(S) : Robinson et al.

It is certified that error appears in the above-identified patent and that said Letters Patent is hereby corrected as shown below:

Column 31, line 6, change "A of nucleotide" to --Nucleotide--.

Column 31, line 17, change "host" to --host cell--.

Column 31, line 25, change "cell" to --host cell--.

Column 31, lines 25-26, delete "non-naturally occurring".

Column 31, line 34, change "cell" to --host cell--.

Column 32, lines 14-15, delete "non-naturally occurring".

Column 32, line 24, change "cell" to --host cell--.

Signed and Sealed this

Thirtieth Day of December, 1997

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,643,751
DATED : July 1, 1997
INVENTOR(S) : Robinson et al.

It is certified that error appears in the above-identified patent and that said Letters Patent is hereby corrected as shown below:

Column 7, line 57, change "Ash" to --Asn--.

Column 8, line 21, after "5'-AAAT" underline --AGATCT--; and
line 25, after "5'-GGGC", underline --AAGCTT--.

Column 9, line 50, after "5'-AAAT" underline --AGATCT--; and
line 54, after "5'-GGGC", underline --AAGCTT--.

Column 10, line 38, after "5'-AAATT" underline --AGATCT--; and
line 42, after "5'-GGGC", underline --GGTACC--.

Column 11, line 17, after "5'-AAAT" underline --AGATCT--; and
line 21, after "5'-GGGC", underline --GGTACC--; and
line 62, after "5'-AAAT" underline --AGATCT-- and
line 66, after "5'-GGGC", underline --GGTACC--.

Signed and Sealed this

Seventh Day of April, 1998

Attest:

BRUCE LEHMAN

*Attesting Officer*          *Commissioner of Patents and Trademarks*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1497 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Borrelia burgdorferi
        ( B ) STRAIN: B31

( v i i ) IMMEDIATE SOURCE:
        ( B ) CLONE: pB776

( x i ) SEQUENCE DESCRIPTION: SEQ ID NO:1:

```
ATGAGTTTTG  TGGTCATTAT  TCCCGCGCGC  TACGCGTCGA  CGCGTCTGCC      50

CGGTAAACCA  TTGGTTGATA  TTAACGGCAA  ACCATGATT   GTTCATGTTC     100

TTGAACGCGC  GCGTGAATCA  GGTGCCGAGC  GCATCATCGT  GGCAACCGAT     150

CATGAGGATG  TTGCCCGCGC  CGTTGAAGCC  GCTGGCGGTG  AAGTATGTAT     200

GACGCGCGCC  GATCATCAGT  CAGGAACAGA  ACGTCTGGCG  GAAGTTGTCG     250

AAAAATGCGC  ATTCAGCGAC  GACACGGTGA  TCGTTAATGT  GCAGGGTGAT     300
```

```
GAACCGATGA  TCCCTGCGAC  AATCATTCGT  CAGGTTGCTG  ATAACCTCGC   350

TCAGCGTCAG  GTGGGTATGG  CGACTCTGGC  GGTGCCAATC  CACAATGCGG   400

AAGAAGCGTT  TAACCCGAAT  GCGGTGAAAG  TGGTTCTCGA  CGCTGAAGGG   450

TATGCACTGT  ACTTCTCTCG  CGCCACCATT  CCTTGGGATC  GTGATCGTTT   500

TGCAGAAGGC  CTTGAAACCG  TTGGCGATAA  CTTCCTGCGT  CATCTTGGTA   550

TTTATGGCTA  CCGTGCAGGC  TTTATCCGTC  GTTACGTCAA  CTGGCAGCCA   600

AGTCCGTTAG  AACACATCGA  AATGTTAGAG  CAGCTTCGTG  TTCTGTGGTA   650

CGGCGAAAAA  ATCCATGTTG  CTGTTGCTCA  GGAAGTTCCT  GGCACAGGTG   700

TGGATACCCC  TGAAAATCCG  TCGACAGGGC  TTATGAAGAT  CTCAGACCCG   750

AGAAATACTT  CAAAGGCTAT  TAATTTATT   CAGACAACAG  AAGGGAATTT   800

AAATGAAGTA  GAAAAAGTCT  TAGTAAGAAT  GAAGGAATTG  GCAGTTCAAT   850

CAGGTAACGG  CACATATTCA  GATGCAGACA  GAGGTTCTAT  ACAAATTGAA   900

ATAGAGCAAC  TTACAGACGA  AATTAATAGA  ATTGCTGATC  AAGCTCAATA   950

TAACCAAATG  CACATGTTAT  CAAACAAATC  TGCTTCTCAA  AATGTAAGAA  1000

CAGCTGAAGA  GCTTGGAATG  CAGCCTGCAA  AAATTAACAC  ACCAGCATCG  1050

CTTTCAGGGT  CTCAAGCGTC  TTGGACTTTA  AGAGTTCATG  TTGGAGCAAA  1100

CCAAGATGAA  GCTATTGCTG  TAAATATTTA  TGCAGCTAAT  GTTGCAAATC  1150

TTTTCTCTGG  TGAGGGAGCT  CAAACTGCTC  AGGCTGCACC  GGTTCAAGAG  1200

GGTGTTCAAC  AGGAAGGAGC  TCAACAGCCA  GCACCTGCTA  CAGCACCTTC  1250

TCAAGGCGGA  GTTAATTCTC  CTGTTAATGT  TACAACTACA  GTTGATGCTA  1300

ATACATCACT  TGCTAAAATT  GAAATGCTA   TTAGAATGAT  AAGTGATCAA  1350

AGAGCAAATT  TAGGTGCTTT  CCAAATAGA   CTTGAATCTA  TAAAGGATAG  1400

TACTGAGTAT  GCAATTGAAA  ATCTAAAAGC  ATCTTATGCT  CAAATAAAAG  1450

ATGCTACAAT  GACAGATGAG  GTTGTAGCAG  CAACAACTAA  TAGTTAA     1497
```

( 2 ) INFORMATION FOR SEQ ID NO:2:

( i ) SEQUENCE CHARACTERISTICS:
        ( A ) LENGTH: 499 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Borrelia burgdorferi
        ( B ) STRAIN: B31

( x i ) SEQUENCE DESCRIPTION: SEQ ID NO:2:

```
Met  Ser  Phe  Val  Val  Ile  Ile  Pro  Ala  Arg  Tyr  Ala  Ser  Thr  Arg
 1              5                        10                       15

Leu  Pro  Gly  Lys  Pro  Leu  Val  Asp  Ile  Asn  Gly  Lys  Pro  Met  Ile
               20                       25                       30

Val  His  Val  Leu  Glu  Arg  Ala  Arg  Glu  Ser  Gly  Ala  Glu  Arg  Ile
                    35                       40                       45

Ile  Val  Ala  Thr  Asp  His  Glu  Asp  Val  Ala  Arg  Ala  Val  Glu  Ala
```

|   |   |   |   | 50 |   |   |   |   | 55 |   |   |   | 60 |
|---|---|---|---|----|---|---|---|---|----|---|---|---|----|

Ala Gly Gly Glu Val Cys Met Thr Arg Ala Asp His Gln Ser Gly
                65                      70                  75

Thr Glu Arg Leu Ala Glu Val Val Glu Lys Cys Ala Phe Ser Asp
                80                      85                  90

Asp Thr Val Ile Val Asn Val Gln Gly Asp Glu Pro Met Ile Pro
                95                     100                 105

Ala Thr Ile Ile Arg Gln Val Ala Asp Asn Leu Ala Gln Arg Gln
                110                    115                 120

Val Gly Met Ala Thr Leu Ala Val Pro Ile His Asn Ala Glu Glu
                125                    130                 135

Ala Phe Asn Pro Asn Ala Val Lys Val Leu Asp Ala Glu Gly
                140                    145                 150

Tyr Ala Leu Tyr Phe Ser Arg Ala Thr Ile Pro Trp Asp Arg Asp
                155                    160                 165

Arg Phe Ala Glu Gly Leu Glu Thr Val Gly Asp Asn Phe Leu Arg
                170                    175                 180

His Leu Gly Ile Tyr Gly Tyr Arg Ala Gly Phe Ile Arg Arg Tyr
                185                    190                 195

Val Asn Trp Gln Pro Ser Pro Leu Glu His Ile Glu Met Leu Glu
                200                    205                 210

Gln Leu Arg Val Leu Trp Tyr Gly Glu Lys Ile His Val Ala Val
                215                    220                 225

Ala Gln Glu Val Pro Gly Thr Gly Val Asp Thr Pro Glu Asn Pro
                230                    235                 240

Ser Thr Gly Leu Met Lys Ile Ser Asp Pro Arg Asn Thr Ser Lys
                245                    250                 255

Ala Ile Asn Phe Ile Gln Thr Thr Glu Gly Asn Leu Asn Glu Val
                260                    265                 270

Glu Lys Val Leu Val Arg Met Lys Glu Leu Ala Val Gln Ser Gly
                275                    280                 285

Asn Gly Thr Tyr Ser Asp Ala Asp Arg Gly Ser Ile Gln Ile Glu
                290                    295                 300

Ile Glu Gln Leu Thr Asp Glu Ile Asn Arg Ile Ala Asp Gln Ala
                305                    310                 315

Gln Tyr Asn Gln Met His Met Leu Ser Asn Lys Ser Ala Ser Gln
                320                    325                 330

Asn Val Arg Thr Ala Glu Glu Leu Gly Met Gln Pro Ala Lys Ile
                335                    340                 345

Asn Thr Pro Ala Ser Leu Ser Gly Ser Gln Ala Ser Trp Thr Leu
                350                    355                 360

Arg Val His Val Gly Ala Asn Gln Asp Glu Ala Ile Ala Val Asn
                365                    370                 375

Ile Tyr Ala Ala Asn Val Ala Asn Leu Phe Ser Gly Glu Gly Ala
                380                    385                 390

Gln Thr Ala Gln Ala Ala Pro Val Gln Glu Gly Val Gln Gln Glu
                395                    400                 405

Gly Ala Gln Gln Pro Ala Pro Thr Ala Pro Ser Gln Gly Gly
                410                    415                 420

Val Asn Ser Pro Val Asn Val Thr Thr Val Asp Ala Asn Thr
                425                    430                 435

Ser Leu Ala Lys Ile Glu Asn Ala Ile Arg Met Ile Ser Asp Gln
                440                    445                 450

| Arg | Ala | Asn | Leu | Gly 455 | Ala | Phe | Gln | Asn | Arg 460 | Leu | Glu | Ser | Ile | Lys 465 |

| Asp | Ser | Thr | Glu | Tyr 470 | Ala | Ile | Glu | Asn | Leu 475 | Lys | Ala | Ser | Tyr | Ala 480 |

| Gln | Ile | Lys | Asp | Ala 485 | Thr | Met | Thr | Asp | Glu 490 | Val | Val | Ala | Ala | Thr 495 |

Thr Asn Ser Xaa ( 2 ) INFORMATION FOR SEQ ID NO:3:

( i ) SEQUENCE CHARACTERISTICS:
        ( A ) LENGTH: 747 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Borrelia burgdorferi
        ( B ) STRAIN: B31

( v i i ) IMMEDIATE SOURCE:
        ( B ) CLONE: 776

( x i ) SEQUENCE DESCRIPTION: SEQ ID NO:3:

| AGAAATACTT | CAAAGGCTAT | TAATTTTATT | CAGACAACAG | AAGGGAATTT | 50 |
| AAATGAAGTA | GAAAAAGTCT | TAGTAAGAAT | GAAGGAATTG | GCAGTTCAAT | 100 |
| CAGGTAACGG | CACATATTCA | GATGCAGACA | GAGGTTCTAT | ACAAATTGAA | 150 |
| ATAGAGCAAC | TTACAGACGA | AATTAATAGA | ATTGCTGATC | AAGCTCAATA | 200 |
| TAACCAAATG | CACATGTTAT | CAAACAAATC | TGCTTCTCAA | AATGTAAGAA | 250 |
| CAGCTGAAGA | GCTTGGAATG | CAGCCTGCAA | AAATTAACAC | ACCAGCATCG | 300 |
| CTTTCAGGGT | CTCAAGCGTC | TTGGACTTTA | AGAGTTCATG | TTGGAGCAAA | 350 |
| CCAAGATGAA | GCTATTGCTG | TAAATATTTA | TGCAGCTAAT | GTTGCAAATC | 400 |
| TTTTCTCTGG | TGAGGGAGCT | CAAACTGCTC | AGGCTGCACC | GGTTCAAGAG | 450 |
| GGTGTTCAAC | AGGAAGGAGC | TCAACAGCCA | GCACCTGCTA | CAGCACCTTC | 500 |
| TCAAGGCGGA | GTTAATTCTC | CTGTTAATGT | TACAACTACA | GTTGATGCTA | 550 |
| ATACATCACT | TGCTAAAATT | GAAATGCTA | TTAGAATGAT | AAGTGATCAA | 600 |
| AGAGCAAATT | TAGGTGCTTT | CCAAAATAGA | CTTGAATCTA | TAAAGGATAG | 650 |
| TACTGAGTAT | GCAATTGAAA | ATCTAAAAGC | ATCTTATGCT | CAAATAAAAG | 700 |
| ATGCTACAAT | GACAGATGAG | GTTGTAGCAG | CAACAACTAA | TAGTTAA | 747 |

( 2 ) INFORMATION FOR SEQ ID NO:4:

( i ) SEQUENCE CHARACTERISTICS:
        ( A ) LENGTH: 249 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal (vi) ORIGINAL SOURCE:
  (A) ORGANISM: Borrelia burgdorferi
  (B) STRAIN: B31

(xi) SEQUENCE DESCRIPTION: SEQ ID NO:4:

| Arg | Asn | Thr | Ser | Lys | Ala | Ile | Asn | Phe | Ile | Gln | Thr | Thr | Glu | Gly |
|---|---|---|---|---|---|---|---|---|---|---|---|---|---|---|
| 1 | | | | 5 | | | | | 10 | | | | | 15 |
| Asn | Leu | Asn | Glu | Val | Glu | Lys | Val | Leu | Val | Arg | Met | Lys | Glu | Leu |
| | | | | 20 | | | | | 25 | | | | | 30 |
| Ala | Val | Gln | Ser | Gly | Asn | Gly | Thr | Tyr | Ser | Asp | Ala | Asp | Arg | Gly |
| | | | | 35 | | | | | 40 | | | | | 45 |
| Ser | Ile | Gln | Ile | Glu | Ile | Glu | Gln | Leu | Thr | Asp | Glu | Ile | Asn | Arg |
| | | | | 50 | | | | | 55 | | | | | 60 |
| Ile | Ala | Asp | Gln | Ala | Gln | Tyr | Asn | Gln | Met | His | Met | Leu | Ser | Asn |
| | | | | 65 | | | | | 70 | | | | | 75 |
| Lys | Ser | Ala | Ser | Gln | Asn | Val | Arg | Thr | Ala | Glu | Glu | Leu | Gly | Met |
| | | | | 80 | | | | | 85 | | | | | 90 |
| Gln | Pro | Ala | Lys | Ile | Asn | Thr | Pro | Ala | Ser | Leu | Ser | Gly | Ser | Gln |
| | | | | 95 | | | | | 100 | | | | | 105 |
| Ala | Ser | Trp | Thr | Leu | Arg | Val | His | Val | Gly | Ala | Asn | Gln | Asp | Glu |
| | | | | 110 | | | | | 115 | | | | | 120 |
| Ala | Ile | Ala | Val | Asn | Ile | Tyr | Ala | Ala | Asn | Val | Ala | Asn | Leu | Phe |
| | | | | 125 | | | | | 130 | | | | | 135 |
| Ser | Gly | Glu | Gly | Ala | Gln | Thr | Ala | Gln | Ala | Ala | Pro | Val | Gln | Glu |
| | | | | 140 | | | | | 145 | | | | | 150 |
| Gly | Val | Gln | Gln | Glu | Gly | Ala | Gln | Gln | Pro | Ala | Pro | Ala | Thr | Ala |
| | | | | 155 | | | | | 160 | | | | | 165 |
| Pro | Ser | Gln | Gly | Gly | Val | Asn | Ser | Pro | Val | Asn | Val | Thr | Thr | Thr |
| | | | | 170 | | | | | 175 | | | | | 180 |
| Val | Asp | Ala | Asn | Thr | Ser | Leu | Ala | Lys | Ile | Glu | Asn | Ala | Ile | Arg |
| | | | | 185 | | | | | 190 | | | | | 195 |
| Met | Ile | Ser | Asp | Gln | Arg | Ala | Asn | Leu | Gly | Ala | Phe | Gln | Asn | Arg |
| | | | | 200 | | | | | 205 | | | | | 210 |
| Leu | Glu | Ser | Ile | Lys | Asp | Ser | Thr | Glu | Tyr | Ala | Ile | Glu | Asn | Leu |
| | | | | 215 | | | | | 220 | | | | | 225 |
| Lys | Ala | Ser | Tyr | Ala | Gln | Ile | Lys | Asp | Ala | Thr | Met | Thr | Asp | Glu |
| | | | | 230 | | | | | 235 | | | | | 240 |
| Val | Val | Ala | Ala | Thr | Thr | Asn | Ser | Xaa | | | | | | |
| | | | | 245 | | | | | | | | | | |

(2) INFORMATION FOR SEQ ID NO:5:

(i) SEQUENCE CHARACTERISTICS:
    (A) LENGTH: 1131 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Borrelia burgdorferi
    (B) STRAIN: B31

(vii) IMMEDIATE SOURCE:
    (B) CLONE: pb410

( x i ) SEQUENCE DESCRIPTION: SEQ ID NO:5:

| | | | | |
|---|---|---|---|---|
| ATGAGTTTTG | TGGTCATTAT | TCCCGCGCGC | TACGCGTCGA | CGCGTCTGCC | 50
| CGGTAAACCA | TTGGTTGATA | TTAACGGCAA | ACCCATGATT | GTTCATGTTC | 100
| TTGAACGCGC | GCGTGAATCA | GGTGCCGAGC | GCATCATCGT | GGCAACCGAT | 150
| CATGAGGATG | TTGCCCGCGC | CGTTGAAGCC | GCTGGCGGTG | AAGTATGTAT | 200
| GACGCGCGCC | GATCATCAGT | CAGGAACAGA | ACGTCTGGCG | GAAGTTGTCG | 250
| AAAAATGCGC | ATTCAGCGAC | GACACGGTGA | TCGTTAATGT | GCAGGGTGAT | 300
| GAACCGATGA | TCCCTGCGAC | AATCATTCGT | CAGGTTGCTG | ATAACCTCGC | 350
| TCAGCGTCAG | GTGGGTATGG | CGACTCTGGC | GGTGCCAATC | CACAATGCGG | 400
| AAGAAGCGTT | TAACCCGAAT | GCGGTGAAAG | TGGTTCTCGA | CGCTGAAGGG | 450
| TATGCACTGT | ACTTCTCTCG | CGCCACCATT | CCTTGGGATC | GTGATCGTTT | 500
| TGCAGAAGGC | CTTGAAACCG | TTGGCGATAA | CTTCCTGCGT | CATCTTGGTA | 550
| TTTATGGCTA | CCGTGCAGGC | TTTATCCGTC | GTTACGTCAA | CTGGCAGCCA | 600
| AGTCCGTTAG | AACACATCGA | AATGTTAGAG | CAGCTTCGTG | TTCTGTGGTA | 650
| CGGCGAAAAA | ATCCATGTTG | CTGTTGCTCA | GGAAGTTCCT | GGCACAGGTG | 700
| TGGATACCCC | TGAAAATCCG | TCGACAGGGC | TTATGAAGAT | CTCAGACCCG | 750
| TCAAACAAAT | CTGCTTCTCA | AATGTAAGA | ACAGCTGAAG | AGCTTGGAAT | 800
| GCAGCCTGCA | AAAATTAACA | CACCAGCATC | GCTTTCAGGG | TCTCAAGCGT | 850
| CTTGGACTTT | AAGAGTTCAT | GTTGGAGCAA | ACCAAGATGA | AGCTATTGCT | 900
| GTAAATATTT | ATGCAGCTAA | TGTTGCAAAT | CTTTTCTCTG | GTGAGGGAGC | 950
| TCAAACTGCT | CAGGCTGCAC | CGGTTCAAGA | GGGTGTTCAA | CAGGAAGGAG | 1000
| CTCAACAGCC | AGCACCTGCT | ACAGCACCTT | CTCAAGGCGG | AGTTAATTCT | 1050
| CCTGTTAATG | TTACAACTAC | AGTTGATGCT | AATACATCAC | TTGCTAAAAT | 1100
| TGAAAATGCT | ATTAGAATGA | TAAGTGATTA | A | | 1131

( 2 ) INFORMATION FOR SEQ ID NO:6:

( i ) SEQUENCE CHARACTERISTICS:
        ( A ) LENGTH: 377 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Borrelia burgdorferi
        ( B ) STRAIN: B31

( x i ) SEQUENCE DESCRIPTION: SEQ ID NO:6:

```
Met Ser Phe Val Val Ile Ile Pro Ala Arg Tyr Ala Ser Thr Arg
 1               5                  10                  15

Leu Pro Gly Lys Pro Leu Val Asp Ile Asn Gly Lys Pro Met Ile
                20                  25                  30

Val His Val Leu Glu Arg Ala Arg Glu Ser Gly Ala Glu Arg Ile
                35                  40                  45

Ile Val Ala Thr Asp His Glu Asp Val Ala Arg Ala Val Glu Ala
```

|    |     |     |     |     |     |     |     |     |     |     |     |     |     |
|----|-----|-----|-----|-----|-----|-----|-----|-----|-----|-----|-----|-----|-----|
|    |     |     |     | 50  |     |     |     |     | 55  |     |     |     | 60  |
| Ala | Gly | Gly | Glu | Val | Cys | Met | Thr | Arg | Ala | Asp | His | Gln | Ser | Gly |
|    |     |     |     | 65  |     |     |     |     | 70  |     |     |     | 75  |
| Thr | Glu | Arg | Leu | Ala | Glu | Val | Val | Glu | Lys | Cys | Ala | Phe | Ser | Asp |
|    |     |     |     | 80  |     |     |     |     | 85  |     |     |     | 90  |
| Asp | Thr | Val | Ile | Val | Asn | Val | Gln | Gly | Asp | Glu | Pro | Met | Ile | Pro |
|    |     |     |     | 95  |     |     |     |     | 100 |     |     |     | 105 |
| Ala | Thr | Ile | Ile | Arg | Gln | Val | Ala | Asp | Asn | Leu | Ala | Gln | Arg | Gln |
|    |     |     |     | 110 |     |     |     |     | 115 |     |     |     | 120 |
| Val | Gly | Met | Ala | Thr | Leu | Ala | Val | Pro | Ile | His | Asn | Ala | Glu | Glu |
|    |     |     |     | 125 |     |     |     |     | 130 |     |     |     | 135 |
| Ala | Phe | Asn | Pro | Asn | Ala | Val | Lys | Val | Val | Leu | Asp | Ala | Glu | Gly |
|    |     |     |     | 140 |     |     |     |     | 145 |     |     |     | 150 |
| Tyr | Ala | Leu | Tyr | Phe | Ser | Arg | Ala | Thr | Ile | Pro | Trp | Asp | Arg | Asp |
|    |     |     |     | 155 |     |     |     |     | 160 |     |     |     | 165 |
| Arg | Phe | Ala | Glu | Gly | Leu | Glu | Thr | Val | Gly | Asp | Asn | Phe | Leu | Arg |
|    |     |     |     | 170 |     |     |     |     | 175 |     |     |     | 180 |
| His | Leu | Gly | Ile | Tyr | Gly | Tyr | Arg | Ala | Gly | Phe | Ile | Arg | Arg | Tyr |
|    |     |     |     | 185 |     |     |     |     | 190 |     |     |     | 195 |
| Val | Asn | Trp | Gln | Pro | Ser | Pro | Leu | Glu | His | Ile | Glu | Met | Leu | Glu |
|    |     |     |     | 200 |     |     |     |     | 205 |     |     |     | 210 |
| Gln | Leu | Arg | Val | Leu | Trp | Tyr | Gly | Glu | Lys | Ile | His | Val | Ala | Val |
|    |     |     |     | 215 |     |     |     |     | 220 |     |     |     | 225 |
| Ala | Gln | Glu | Val | Pro | Gly | Thr | Gly | Val | Asp | Thr | Pro | Glu | Asn | Pro |
|    |     |     |     | 230 |     |     |     |     | 235 |     |     |     | 240 |
| Ser | Thr | Gly | Leu | Met | Lys | Ile | Ser | Asp | Pro | Ser | Asn | Lys | Ser | Ala |
|    |     |     |     | 245 |     |     |     |     | 250 |     |     |     | 255 |
| Ser | Gln | Asn | Val | Arg | Thr | Ala | Glu | Glu | Leu | Gly | Met | Gln | Pro | Ala |
|    |     |     |     | 260 |     |     |     |     | 265 |     |     |     | 270 |
| Lys | Ile | Asn | Thr | Pro | Ala | Ser | Leu | Ser | Gly | Ser | Gln | Ala | Ser | Trp |
|    |     |     |     | 275 |     |     |     |     | 280 |     |     |     | 285 |
| Thr | Leu | Arg | Val | His | Val | Gly | Ala | Asn | Gln | Asp | Glu | Ala | Ile | Ala |
|    |     |     |     | 290 |     |     |     |     | 295 |     |     |     | 300 |
| Val | Asn | Ile | Tyr | Ala | Ala | Asn | Val | Ala | Asn | Leu | Phe | Ser | Gly | Glu |
|    |     |     |     | 305 |     |     |     |     | 310 |     |     |     | 315 |
| Gly | Ala | Gln | Thr | Ala | Gln | Ala | Ala | Pro | Val | Gln | Glu | Gly | Val | Gln |
|    |     |     |     | 320 |     |     |     |     | 325 |     |     |     | 330 |
| Gln | Glu | Gly | Ala | Gln | Gln | Pro | Ala | Pro | Ala | Thr | Ala | Pro | Ser | Gln |
|    |     |     |     | 335 |     |     |     |     | 340 |     |     |     | 345 |
| Gly | Gly | Val | Asn | Ser | Pro | Val | Asn | Val | Thr | Thr | Thr | Val | Asp | Ala |
|    |     |     |     | 350 |     |     |     |     | 355 |     |     |     | 360 |
| Asn | Thr | Ser | Leu | Ala | Lys | Ile | Glu | Asn | Ala | Ile | Arg | Met | Ile | Ser |
|    |     |     |     | 365 |     |     |     |     | 370 |     |     |     | 375 |
| Asp | Xaa |     |     |     |     |     |     |     |     |     |     |     |     |

( 2 ) INFORMATION FOR SEQ ID NO:7:

( i ) SEQUENCE CHARACTERISTICS:
        ( A ) LENGTH: 381 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO (iv) ANTI-SENSE: NO (vi) ORIGINAL SOURCE:
    (A) ORGANISM: Borrelia burgdorferi
    (B) STRAIN: B31

(vii) IMMEDIATE SOURCE:
    (B) CLONE: 410

(xi) SEQUENCE DESCRIPTION: SEQ ID NO:7:

```
TCAAACAAAT CTGCTTCTCA AAATGTAAGA ACAGCTGAAG AGCTTGGAAT      50
GCAGCCTGCA AAAATTAACA CACCAGCATC GCTTTCAGGG TCTCAAGCGT     100
CTTGGACTTT AAGAGTTCAT GTTGGAGCAA ACCAAGATGA AGCTATTGCT     150
GTAAATATTT ATGCAGCTAA TGTTGCAAAT CTTTTCTCTG GTGAGGGAGC     200
TCAAACTGCT CAGGCTGCAC CGGTTCAAGA GGGTGTTCAA CAGGAAGGAG     250
CTCAACAGCC AGCACCTGCT ACAGCACCTT CTCAAGGCGG AGTTAATTCT     300
CCTGTTAATG TTACAACTAC AGTTGATGCT AATACATCAC TTGCTAAAAT     350
TGAAAATGCT ATTAGAATGA TAAGTGATTA A                         381
```

(2) INFORMATION FOR SEQ ID NO:8:

(i) SEQUENCE CHARACTERISTICS:
        (A) LENGTH: 127 amino acids
        (B) TYPE: amino acid
        (D) TOPOLOGY: linear (ii) MOLECULE TYPE: Protein (iii) HYPOTHETICAL:

(iv) ANTI-SENSE: NO (v) FRAGMENT TYPE: internal (vi) ORIGINAL SOURCE:
        (A) ORGANISM: Borrelia burgdorferi
        (B) STRAIN: B31

(xi) SEQUENCE DESCRIPTION: SEQ ID NO:8:

```
Ser Asn Lys Ser Ala Ser Gln Asn Val Arg Thr Ala Glu Glu Leu
  1               5                  10                  15
Gly Met Gln Pro Ala Lys Ile Asn Thr Pro Ala Ser Leu Ser Gly
                 20                  25                  30
Ser Gln Ala Ser Trp Thr Leu Arg Val His Val Gly Ala Asn Gln
                 35                  40                  45
Asp Glu Ala Ile Ala Val Asn Ile Tyr Ala Ala Asn Val Ala Asn
                 50                  55                  60
Leu Phe Ser Gly Glu Gly Ala Gln Thr Ala Gln Ala Ala Pro Val
                 65                  70                  75
Gln Glu Gly Val Gln Gln Glu Gly Ala Gln Gln Pro Ala Pro Ala
                 80                  85                  90
Thr Ala Pro Ser Gln Gly Gly Val Asn Ser Pro Val Asn Val Thr
                 95                 100                 105
Thr Thr Val Asp Ala Asn Thr Ser Leu Ala Lys Ile Glu Asn Ala
                110                 115                 120
Ile Arg Met Ile Ser Asp Xaa
                125
```